US010744505B2

(12) United States Patent
Ponomarenko (10) Patent No.: US 10,744,505 B2
(45) Date of Patent: Aug. 18, 2020

(54) MICROFLUIDIC DEVICE FOR IN VITRO 3D CELL CULTURE EXPERIMENTATION

(71) Applicant: InteCrypt B.V., 's-Hertogenbosch (NL)

(72) Inventor: Mikhail Alexandrovich Ponomarenko, 's-Hertogenbosch (NL)

(73) Assignee: INTECRYPT B.V., 'S-Hertogenbosch (NL)

( * ) Notice: Subject to any disclaimer, the term of this patent is extended or adjusted under 35 U.S.C. 154(b) by 119 days.

(21) Appl. No.: 15/575,136

(22) PCT Filed: May 20, 2016

(86) PCT No.: PCT/NL2016/050361
§ 371 (c)(1),
(2) Date: Nov. 17, 2017

(87) PCT Pub. No.: WO2016/186503
PCT Pub. Date: Nov. 24, 2016

(65) Prior Publication Data
US 2018/0141047 A1    May 24, 2018

(30) Foreign Application Priority Data
May 21, 2015 (NL) ..................... 2014840

(51) Int. Cl.
*B01L 3/00* (2006.01)
*C12M 3/06* (2006.01)
(Continued)

(52) U.S. Cl.
CPC ... *B01L 3/502761* (2013.01); *B01L 3/502753* (2013.01); *C12M 23/16* (2013.01);
(Continued)

(58) Field of Classification Search
CPC ......... B01L 3/502761; B01L 3/502753; B01L 2300/0829; B01L 2300/165;
(Continued)

(56) References Cited

U.S. PATENT DOCUMENTS

2013/0295598 A1* 11/2013 Marx ..................... C12M 21/08
435/29
2014/0057311 A1* 2/2014 Kamm ............. B01L 3/502753
435/29
(Continued)

FOREIGN PATENT DOCUMENTS

WO    2015032889 A1    3/2015

OTHER PUBLICATIONS

Tran, Trong Binh, Sungbo Cho, and Junhong Min. "Hydrogel-based diffusion chip with Electric Cell-substrate Impedance Sensing (ECIS) integration for cell viability assay and drug toxicity screening." Biosensors and Bioelectronics 50 (2013): 453-459.
(Continued)

*Primary Examiner* — Michael L Hobbs
(74) *Attorney, Agent, or Firm* — Hoffmann & Baron, LLP (57) ABSTRACT

A microfluidic device for in vitro 3D cell culture experimentation comprises a body in which is provided a cell culture chamber that is at least partly filled with a scaffolding substance for maintaining a cell culture. In the body a fluid path is provided that communicates with the cell culture chamber for directing a fluid stream along the scaffolding substance. The culture chamber above the scaffolding substance opens into an access port which is provided at an outer top surface of the body to provide direct access to the scaffolding substance. The scaffolding substance forms a fluid flow barrier which separates the fluid path from the access port.

21 Claims, 6 Drawing Sheets

(51) Int. Cl.
    *C12M 1/34*     (2006.01)
    *C12N 5/00*     (2006.01)

(52) U.S. Cl.
    CPC ........... C12M 41/32 (2013.01); C12N 5/0062 (2013.01); *B01L 2300/069* (2013.01); *B01L 2300/0829* (2013.01); *B01L 2300/0867* (2013.01); *B01L 2300/0874* (2013.01); *B01L 2300/165* (2013.01); *C12N 2513/00* (2013.01)

(58) Field of Classification Search
    CPC ...... B01L 2300/0874; B01L 2300/069; C12M 41/32; C12M 23/16; C12N 5/0062; C12N 2513/00
    See application file for complete search history.

(56) References Cited

U.S. PATENT DOCUMENTS

2014/0302549 A1    10/2014   Marx
2015/0087006 A1     3/2015   Pak et al.

OTHER PUBLICATIONS

Atencia, Javier, Jayne Morrow, and Laurie E Locascio. "The microfluidic palette: a diffusive gradient generator with spatio-temporal control." Lab on a Chip 9.18 (2009): 2707-2714.

\* cited by examiner

MICROFLUIDIC DEVICE FOR IN VITRO 3D CELL CULTURE EXPERIMENTATION

This application is the U.S. National Phase of, and Applicant claims priority from, International Patent Application Number PCT/NL2016/050361 filed 20 May 2016, which claims priority from NL 2014840 filed 21 May 2015, each of which is incorporated herein by reference.

BACKGROUND OF THE INVENTION

The present invention relates to a microfluidic device for in vitro 3D cell culture experimentation comprising a body in which is provided a cell culture chamber at least partly filled with a scaffolding substance for maintaining a cell culture, and a fluid path communicating with the cell culture chamber for directing a fluid stream along the scaffolding substance. The present invention further relates to a method for in vitro 3D cell culture experimentation, including complex living tissue reconstruction, using the microfluidic device of the present invention.

In vitro cell culture experimentation is important in biological and medical sciences for allowing investigation of cellular behavior of individual cells or of cells as part of larger cell cultures. For instance the investigation of uptake of biomolecules by cells may lead to improved knowledge and understanding of the effect of such biomolecules on a cellular, tissue, organ and subject level, which in turn may lead for example to the development of personalized medicine. Currently pharmacokinetic and toxicological evaluation of drug candidates relies largely on costly, labor-intensive, time-consuming and ethically questionable animal test systems, which show only very limited predictive value for clinical efficacy and toxicity.

Many methods and devices for culturing, expanding and differentiating cells in vitro have thus been developed. A conventional and still often used method is growth and maintenance of cells or cell cultures on a suitable growth surface such as a cell culture dish filled with liquid or jellified culture medium. The culture medium may comprise specific constituents which affect the growth and maintenance of the cells or cell culture in desired ways. However the predictive value of these two dimensional (2D) cell culture models for some application may be still very limited, because of the loss of physiological context.

With 3D scaffolds, for example cells incapsulated in a scaffolding substance such as hydrogel, tissue-like connectivity may be achieved, but there are limits in controlling the cell culture conditions. The 3D models mostly lack the complexity required for pharmacokinetic studies. For many applications in such models there is a limited nutrient supply to the cell culture and an accumulation of metabolic waste products that can confound cell responses to drugs. The 3D models also fail to mimic spatiotemporal biochemical gradients existing in vivo, and lack the provision of mechanical cues such as flow, perfusion, pressure, mechanical stress. It is also problematic for real-time imaging, and biochemical analysis can hardly be performed in live cells due to reaction-diffusion phenomena. Furthermore, it is not easily possible to engineer microsystems that integrate multiple organ/tissue mimetics with active vascular conduits and barrier tissues.

Microfluidic devices such as microfluidic chips allow for addressing these limitations. With microfluidic devices fluid flow may be controlled in the micrometer and nanoliter scale in precisely defined geometries. Because of the micro geometrical dimensions, the flow of fluids is laminar, and placement of fluid volumes in very low amounts is possible. The ability of exactly timing fluid flow allows precise chemical and physical control of the microenvironment. For cell cultures in microfluidic devices the doses delivered to cells can be measured in nanoliters or less, representing a significant improvement in precision. Small volume effects of fluids mimic physiological conditions of cells or cell-populations in tissues more appropriately than cells that are cultured in larger volumes. Microfluidic systems also allow detailed analysis of cell migration in a social context. Controlling the spatiotemporal cues of the microenvironment and the ability to shape the geometry of cultured cells for instance allows studying of primary neuronal cells and cell lines in microfluidic chips.

Integration of microfluidics with 3D scaffolding systems renders it possible to adapt culture conditions both biochemically and biomechanically, such as creating dynamic 3D structures, and provides a microenvironment that allows formation of artificial tissues from cultured cells. Microfluidic cell culture devices allow precise control of cell numbers and cell density in a given area or volume, and can provide placement of cells in complex geometries. Because cells can be organized into three-dimensional geometries in scaffolding substances such as hydrogels in the microfluidic devices, it is possible to culture cells in 3D structures resembling those in tissues. Homotypic tissue culture models may be achieved in microfluidic devices as well as heterotypic tissue culture models that mimic the respective tissue closely both from a histologic as well as from a physiological and functional standpoint. This allows for instance for high-throughput pharmacological studies and might result in using microfluidic cell culture systems also for regenerative purposes.

The small dimensions of spatially separated microfluidic compartments in microfluidic cell culture devices allow assembly of a multitude of individually controllable cell cultures in chambers on a single device. This facilitates high parallelization of experiments, high throughput of samples and reactions and thus improvement of reproducibility, as well as a reduction in reagent costs.

Resulting from the above-mentioned advantages, microfluidics has become particularly valuable for analysis of single cell dynamics. With the help of microfluidic devices cell growth and regulation of cell size can be directly observed and lineages of single cells can be tracked for several generations. On a molecular level microfluidics allow the characterization of transcription factor and gene expression dynamics in single-cells thereby adding substantially to our understanding of the function of biological systems.

The presently available microfluidic devices for in vitro 3D cell culture experimentation comprise a closed system to shield the cell culture and the culture conditions from possible outside influences, and provide a limited accessibility to the cell culture grown in the culture chamber of the device. Thus the known devices render the simultaneous manipulation and analysis of cultured cells rather difficult, particularly monitoring of cells in complex geometries with high spatial and temporal resolution and their individual retrieval during or following experiments.

As a result, there is a need for an improved microfluidic system for cell culture investigation which may be particularly applied in drug studies, vaccine development and other types of medical research. The present invention thus provides a new device and method for cell culture investigation, with which it is possible to investigate all types of cells such as vascular cells and organ cells individually or in functional units of tissues and organs in vitro. These and other aspects of the invention are evident from the specification and claims hereinafter.

SUMMARY OF THE INVENTION

In one aspect of the present invention a microfluidic device for in vitro complex living tissue reconstruction is provided. It is proposed that the in vitro complex living tissue reconstructed by the fluidic device of the present invention closely mimics the in vivo tissue of a living multicellular organism such as a plant or animal. The present invention thus provides a microfluidic device for in vitro 3D cell culture experimentation according to the preamble, which microfluidic device is characterized in that the culture chamber above the scaffolding substance opens into an access port provided at an outer top surface of the body for direct access to the scaffolding substance which forms a fluid flow barrier separating the fluid path from the access port. The access port in the device according to the invention provides a direct access to the culture chamber there below. Thus the scaffolding substance may be conveniently provided in the culture chamber through the access port and cells cultured in the device or conditions in the culture chamber may be easily manipulated via the access port. The access port for instance allows easy seeding or retrieval of cells in the culture chamber.

If needed the cell culture environment in the microfluidic device may be closed off from an outside environment by placing a suitable cover or lid over the access port. The cover or lid may be an integral part of the microfluidic device or a separate body. The cover or lid is preferably detachably connected with the body of the microfluidic device, which renders it possible to close or open the access port at any time as desired.

The term 'fluid flow barrier' as used herein refers to any means which forms a restriction for a fluid flow. A fluid flow barrier may be used to redirect a free flow of a fluid to a certain extent. The fluid flow barrier may be a complete restriction in that no flow of fluid there through is allowed, or may be a partial restriction in that some fluid flow there through is possible. The fluid flow barrier may in any event allow movement of the fluid or parts thereof, for example substances, particles, or other components in the fluid, through the fluid flow barrier by means of diffusion. Because of the provision of a scaffolding substance in the culture chamber of the microfluidic device which forms a fluid flow barrier separating the fluid path from the access port, any fluid flowing through the fluid path in the microfluidic device is for a larger part directed along the culture chamber, preventing a strong flow of fluid through the culture chamber. As a consequence only cells exposed on an outside of the scaffolding substance will possibly experience shear stress across the surface, whereas this will not or hardly be the case for a cell culture captured in the scaffolding substance.

The provision of the fluid flow barrier may be used to mimic the mechanical forces that help govern the architecture of tissues such as the lung, bone, articular cartilage, and vascular tissues. Importantly many cell types including fibroblasts, smooth muscle cells, osteocytes, and chondrocytes, reside within a three-dimensional environment and are exposed to interstitial fluid forces. Physiological interstitial flow is the movement of fluid through the extracellular matrix of a tissue, often between blood vessels and lymphatic capillaries. It provides convection necessary for the transport of large proteins through the interstitial space and constitutes an important component of the microcirculation. Interstitial flow also provides a specific mechanical environment to cells in the interstitium that could play an important role in determining interstitial organization and architecture. Thus the microfluidic device according to the invention may employ a scaffolding substance that forms a fluid flow barrier between the fluid flow path and the culture chamber which allows for a flow of fluid from the fluid flow path through the scaffolding substance mimicking that of interstitial flow, in order to expose the cultured cells within the scaffolding substance to interstitial fluid forces and to provide the cells with the necessary or intended nutrients and/or other biomolecules. Types of cells, such as endothelial and epithelial cells, that in tissue form a monolayer to create a lumen or surface and are exposed to shear stresses across the surface, may be seeded on the outside of the scaffolding substance to be exposed to the fluid flow of fluid moving through the fluid flow path of the device.

According to a preferred embodiment the microfluidic device of the present invention is characterized in that the body comprises a set of fluid paths each fluid path communicating with the cell culture chamber for directing a respective fluid stream along the scaffolding substance, wherein the scaffolding substance separates the respective fluid paths. The set of fluid paths, consisting of two, three, four, five or even more fluid paths, in the microfluidic device according to the invention allows for the supply of fluid or components of the fluid to the culture chamber at different locations of the scaffolding substance, thus mimicking a network of supply vessels such as blood vessels and capillary lymph channels for a tissue. Different or identical fluids may be flown through each fluid path in order to supply components of interest such as nutrients, chemicals, signaling proteins and/or other biomolecules and factors, to the cell culture in the culture chamber.

According to a further preferred embodiment the microfluidic device of the present invention is characterized in that the access port is provided directly above the cell culture chamber. Because of such provision of the access port directly above the cell culture chamber, the access port provides an unobstructed view to the cell culture chamber. Thus it is possible to monitor cells in the culture chamber in complex geometries with high spatial and temporal resolution. Additionally, by providing a medium, such as a fluid, in the access port on top of the scaffolding substance, a medium pressure is applied on the scaffolding substance stimulating perfusion of the fluid through the scaffolding substance.

A particular embodiment of the microfluidic device of the present invention is in this respect characterized in that the access port has a height dimension extending between the outer top surface of the body and an opening to the culture chamber which height dimension is larger than a height dimension of the inlet opening of each channel extending between the outer surface of the body and a bottom of the respective channel. For instance the access port may be open at the outer top surface of the body which surface is elevated with respect to an outer surface of the body in which the inlet opening of a channel is provided. The outer surface of the body in which the inlet opening of the channel is provided may be any surface of the body lower positioned than the outer top surface of the body, e.g. a lower horizontal surface, a recessed surface, an angled or vertical side surface of the body etcetera. A column height of fluid applied in the access port may thus differ from that of each fluid applied in the fluid channels of the device. As a result the diffusion and/or perfusion rate of the fluids or fluid components of the fluid channels to the culture chamber may be controlled as desired by applying less or more fluid in the access port.

In a further preferred embodiment the microfluidic device according to the present invention is characterized in that the fluid paths are channels in the body each channel extending between a respective inlet opening at an outer surface of the body and an outlet opening at an outer surface of the body. The channels may direct a fluid flow from the inlet opening along the scaffolding substance to the outlet opening with the fluid being in micro amounts, thus allowing precise control of amounts of fluid or fluid components being supplied to the cell culture in the culture chamber.

A further preferred embodiment of the microfluidic device according to the present invention is characterized in that the body comprises a restricting wall between the access port and the culture chamber, the restricting wall comprising at least one passage opening. The restricting wall poses a means of guidance of a substance applied in the access port to the culture chamber, while providing some protection of the thereunder provided scaffolding substance and cell culture. For instance the access port may be dimensioned such that introduction of the tip of an injection means, such as a syringe or pipette, is possible up to the restricting wall, thus preventing such injection means from affecting an integrity of the scaffolding substance in the culture chamber. Preferably such access port guides the injection means to the passage opening to facilitate the supply of substance or material to the culture chamber. In this respect the microfluidic device of the present invention in a particular embodiment is characterized in that the restricting wall defines a conical shape of the access port.

It is further preferred that the restricting wall between the access port and the culture chamber is positioned above the scaffolding substance leaving a free space above a complete upper surface of the scaffolding substance. Accordingly when the access port is filled with a fluid to apply a fluid pressure to the scaffolding substance, the fluid will accumulate via the at least one passage opening in the restricting wall in the free space above the upper surface of the scaffolding substance to supply the complete surface thereof with the fluid or components of the fluid and to apply an at least almost equal fluid pressure over the complete surface thereof. The term restricting wall as used herein refers to any means with which a cross sectional size of a space in the body defined by the access port and the culture chamber may be restricted locally to define a restricted opening between the access port and the culture. Such means may comprise an integral part of the body facing the space defined by the access port and the culture chamber and extending inward in said space. The means may alternatively or in addition comprise separate means which are provided in the space in the body defined by the access port and the culture chamber.

The access port and the culture chamber of the microfluidic device may be identical in width dimension or may differ in width. Particularly a width of the access port may be narrower or greater than a width of the culture chamber. An access port with a greater width than the culture chamber may be separated from the culture chamber by a restricting wall comprising a passage opening with a width dimension approximately equal to the width of the culture chamber. Accordingly the culture chamber is directly accessible over a complete width thereof through the passage opening, allowing filling and emptying of the whole culture chamber, whereas the broader access port allows for easy guiding of filling material to the passage opening and provides for an unobstructed view of the culture chamber beneath the passage opening.

The culture chamber and fluid paths of the microfluidic device may be of any shape, and may with respect to each other also differ in shape. For instance in a preferred embodiment of the microfluidic device according to the invention one or more of the fluid paths have a smaller or bigger dimension as compared to the other fluid paths, thus allowing for different amounts of fluids being guided to the culture chamber and along the scaffolding substance to mimic different supply channels such as different sized blood vessels and/or lymph capillaries.

In a further preferred embodiment the microfluidic device according to the present invention is characterized in that the scaffolding substance rests on a bottom part of the body opposite the outer top surface. Thus the scaffolding substance after being provided in the culture chamber may be maintained in the culture chamber simply by resting on the bottom part.

A further preferred embodiment of the microfluidic device according to the present invention is characterized in that the fluid paths communicate with the scaffolding substance at a lateral side of the culture chamber. Nutrients or other substances from the fluids flowing through the fluid paths along the lateral sides of the scaffolding substance will diffuse in the scaffolding substance and particularly form a gradient throughout the scaffolding substance in a width direction of the culture chamber. Cells cultured in the scaffolding substance will thus be provided with different amounts of such nutrients or other substances depending particularly on their position in the culture chamber in the width dimension. The effects of such gradient on the resulting cell culture may be easily viewed from above through the access port.

The fluid paths may be dimensioned to communicate with the scaffolding substance over a full height of the scaffolding substance, e.g. a height of each channel defining a fluid path may be identical to a height of the scaffolding substance in the culture chamber or may be identical to a height of the culture chamber. Alternatively the fluid paths may also be configured to communicate with a section of the scaffolding substance, for instance only over a part of the total height of the scaffolding substance in the culture chamber. A height of the channel defining the fluid path may be less than the total height of the scaffolding substance, or the channel may have a height approximately similar to a height of the scaffolding substance, with a restricting element provided between the channel and culture chamber to restrict a communication surface between the fluid path and scaffolding substance. The restricting element may be a further restricting wall, or a column or other shaped part of the body of the microfluidic device. In particular the restricting element is a vertically oriented wall of the body extending between the culture chamber and channel and defining a communication opening there between which communication opening allows fluid communication between the corresponding fluid path and the scaffolding substance.

In a further preferred embodiment the microfluidic device according to the present invention is characterized in that the respective fluid paths communicate with the scaffolding substance at mutual different heights between the bottom part of the body and the outer top surface. Accordingly the different fluid paths may provide nutrients or other substances to the scaffolding substance at different heights, thus creating a third dimension gradient of such nutrients or other substances in the scaffolding substance, to allow investigation of such gradient and the corresponding effect on the cell culture in such third dimension.

According to a further preferred embodiment the microfluidic device of the present invention is characterized in that at least one of the fluid paths has a larger communication area with the scaffolding substance as compared to another of the fluid paths. With a larger communication area between the fluid path and the scaffolding substance it is possible to supply more fluid or components thereof to the cells whereas a smaller communication area may be used for more precise local supply of such fluid or components thereof.

According to a particular embodiment the microfluidic device of the present invention is characterized in that the body comprises at least three fluid paths. In a further particular embodiment the microfluidic device according to the present invention is characterized in that the three fluid paths communicate with the scaffolding substance at a lateral side of the culture chamber at approximately 120 degrees apart. A further particular embodiment of the microfluidic device according to the present invention is characterized in that at least one of the at least three fluid paths communicates with the scaffolding substance at a lower side of the culture chamber opposite the upper side. In this embodiment all geometrical sides of the scaffolding substance in the culture chamber, i.e. the upper, lower, and lateral sides of the scaffolding substance may be provided with nutrients or other substances from fluids flowing through each of the fluid paths and provided in the access port in order to create a complex 3D network of cells mimicking that of in vivo tissue.

In a further preferred embodiment the microfluidic device according to the present invention is characterized in that the fluid paths are separated along at least a part thereof by a wall of the body which wall has a wall end that borders the culture chamber and forms a support structure for the scaffolding substance. The wall end may form a boundary for the scaffolding substance, which prevents the scaffolding substance from escaping from the culture chamber into the fluid paths and possibly completely blocking any of the fluid flows. In a further preferred embodiment the microfluidic device according to the present invention is characterized in that at least the wall end of the wall of the body is of a hydrophobic material. Accordingly the scaffolding substance may be a droplet of a hydrophilic material, such as a hydrophilic liquid, particularly water suitable for cell culture, which is maintained in the culture chamber between the hydrophobic wall ends.

According to a further preferred embodiment the microfluidic device of the present invention is characterized in that at least two wall ends of respective walls separating respective flow paths are positioned with respect to each other to define an imaginary circumference of the culture chamber and in that the scaffolding substance is bound by the imaginary circumference. The imaginary circumference may be of any shape.

According to a particular embodiment the microfluidic device of the present invention is characterized in that the body is a microfluidic chip. A further preferred embodiment of the microfluidic device according to the present invention is characterized in that the microfluidic chip comprises multiple culture chambers and corresponding access ports and fluid paths. The multiple culture chambers and corresponding access ports and fluid paths form separate experimentation units, which allow the microfluidic chip to be used for multiple and/or parallel experiments. Although a chip is a convenient embodiment of the body of the microfluidic device according to the invention, and may for instance conveniently be sized as a standard microscope slide of approximately 75×25×1 mm for convenient visual inspection of the cell culture in the culture chamber by means of a microscope, the body may alternatively be dimensioned as part of a multiwell plate or microplate or for provision in a well of a multiwell plate or microplate, such as for instance a 385 well plate. In such embodiment of the body of the microfluidic device according to the present invention a culture chamber, fluid paths and access port may be provided near a bottom of each of the wells of the well plate. At least part of the height or preferable a complete height of each of the wells may be used to provide a fluid column with fluid pressure on the scaffolding substance with which a perfusion rate in the scaffolding substance may be controlled.

A further preferred embodiment of the microfluidic device according to the present invention is characterized in that at least some of the fluid paths are shared between consecutive culture chambers. Thus the consecutive culture chambers are interconnected through the shared fluid paths and may thus be used to mimic tissue or organs consisting of or comprising separated elements, such as for instance lymph nodes interconnected by lymph capillaries in a lymph system of an individual.

In a further preferred embodiment the microfluidic device according to the present invention is characterized in that the body comprises a top plate with the outer top surface and a separate bottom plate with the bottom part which plates are adhered to each other. The open spaces in the body, including the fluid paths, the culture chamber and the access port may be provided in the outer surface of each or one of the two plates as grooves or recesses, so that the body may then be formed by simply adhering the plates together. In a particular embodiment the microfluidic device according to the present invention is characterized in that the bottom plate is at least almost fully flat. The open spaces are thus provided in the top plate, whereas the almost fully flat bottom plate is a relatively easily produced part with which the open spaces may be closed off by adhering the bottom plate and top plate to each other.

These and other aspects of the present invention are further elucidated by the appended drawings and the corresponding embodiments described hereinafter, which form part of the present application. The drawings are not in any way meant to reflect a limitation of the scope of the invention, unless this is clearly and explicitly indicated.

DETAILED DESCRIPTION

Figure 1:
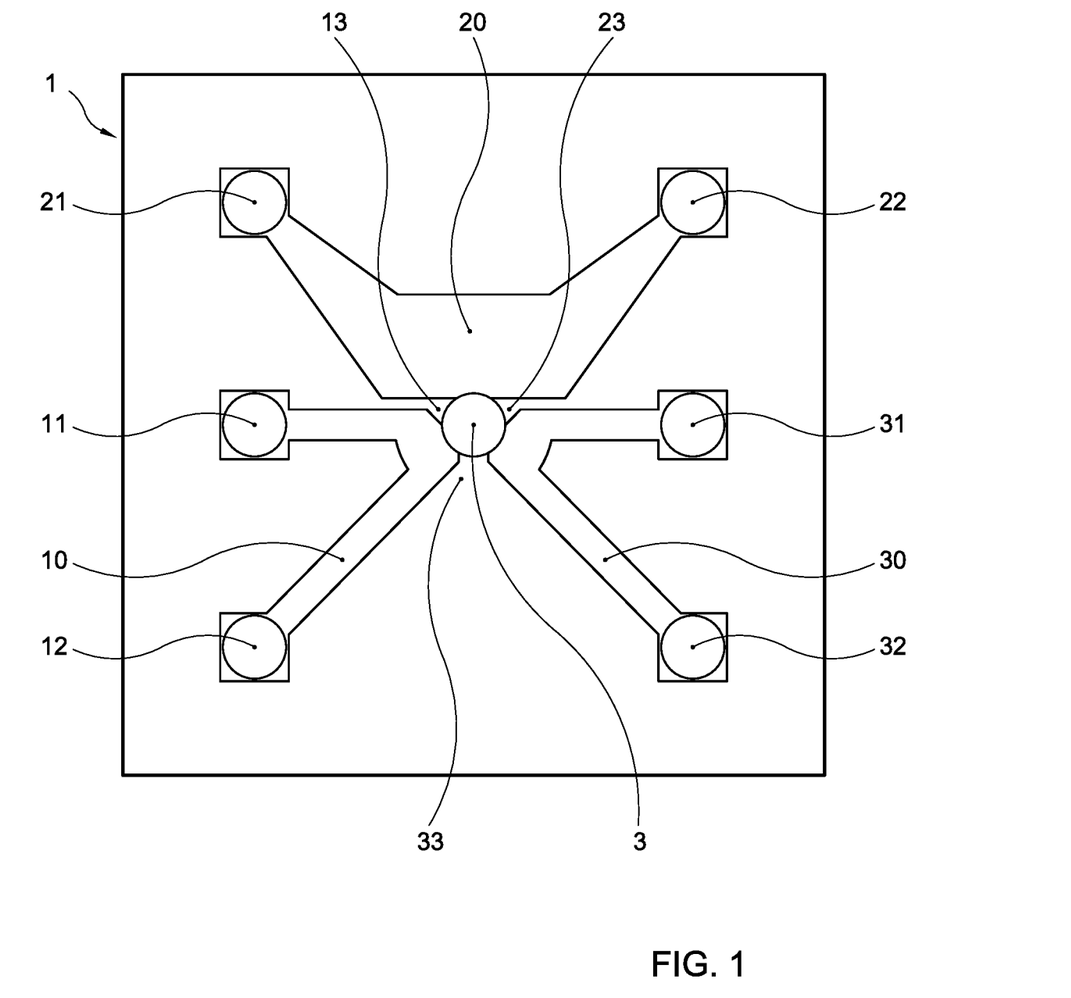
FIG. 1 shows a top view of an embodiment of a microfluidic device according to the invention which may be used for in vitro 3D cell culture experimentation.
Figure 2:
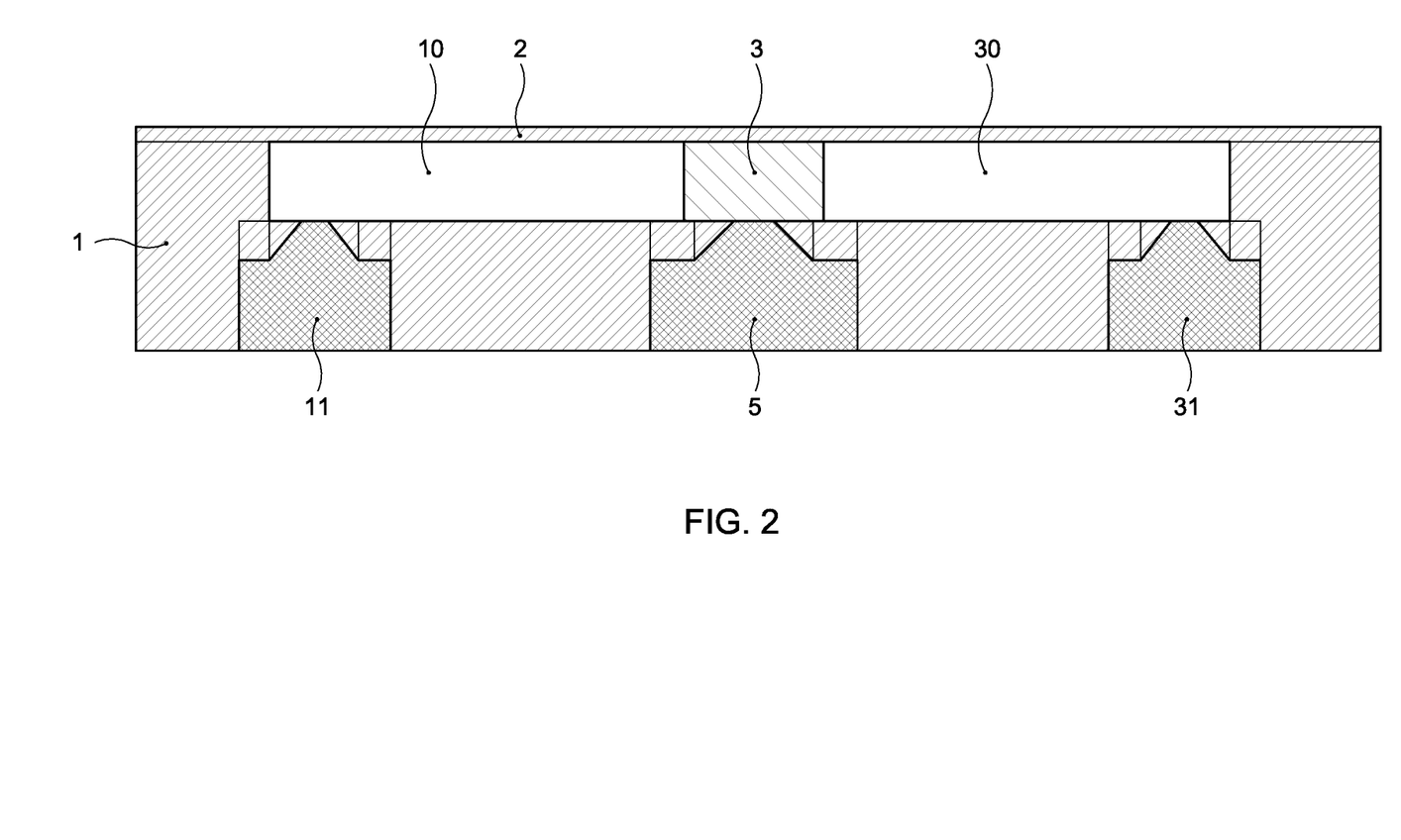
FIG. 2 shows a side view of a cross section of the embodiment of a microfluidic device according to the invention shown in FIG. 1.
Figure 3:
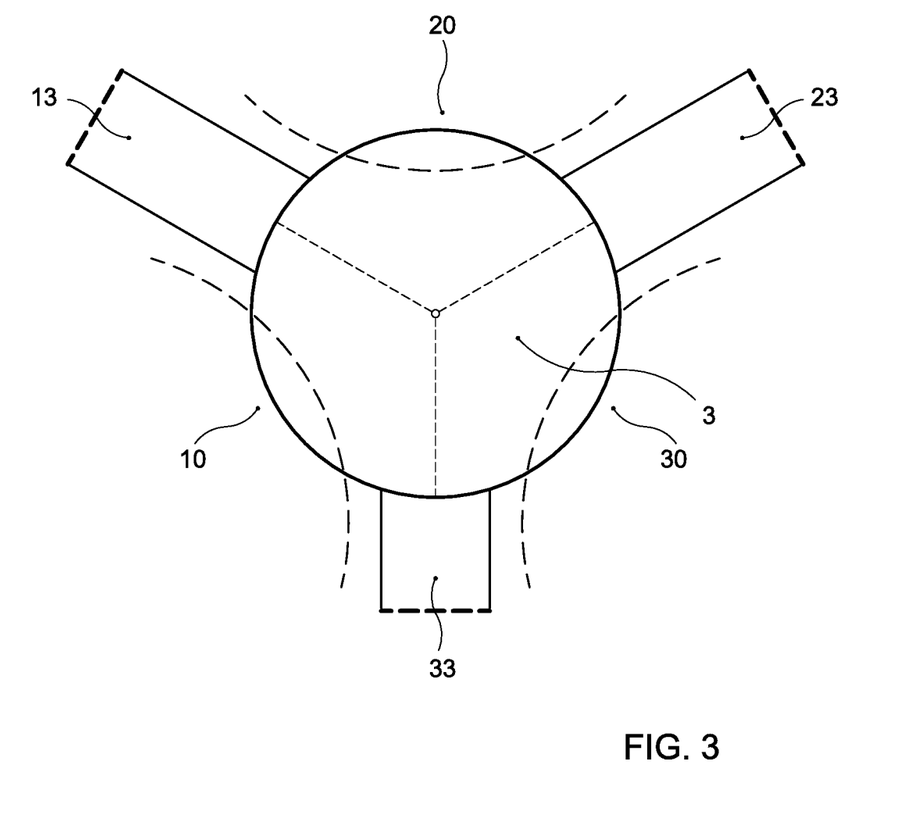
FIG. 3 shows an enlarged schematic view of a culture chamber defined by end walls of the body of the embodiment of the microfluidic device according to the invention as shown in FIG. 1 and FIG. 2.
Figure 4A:
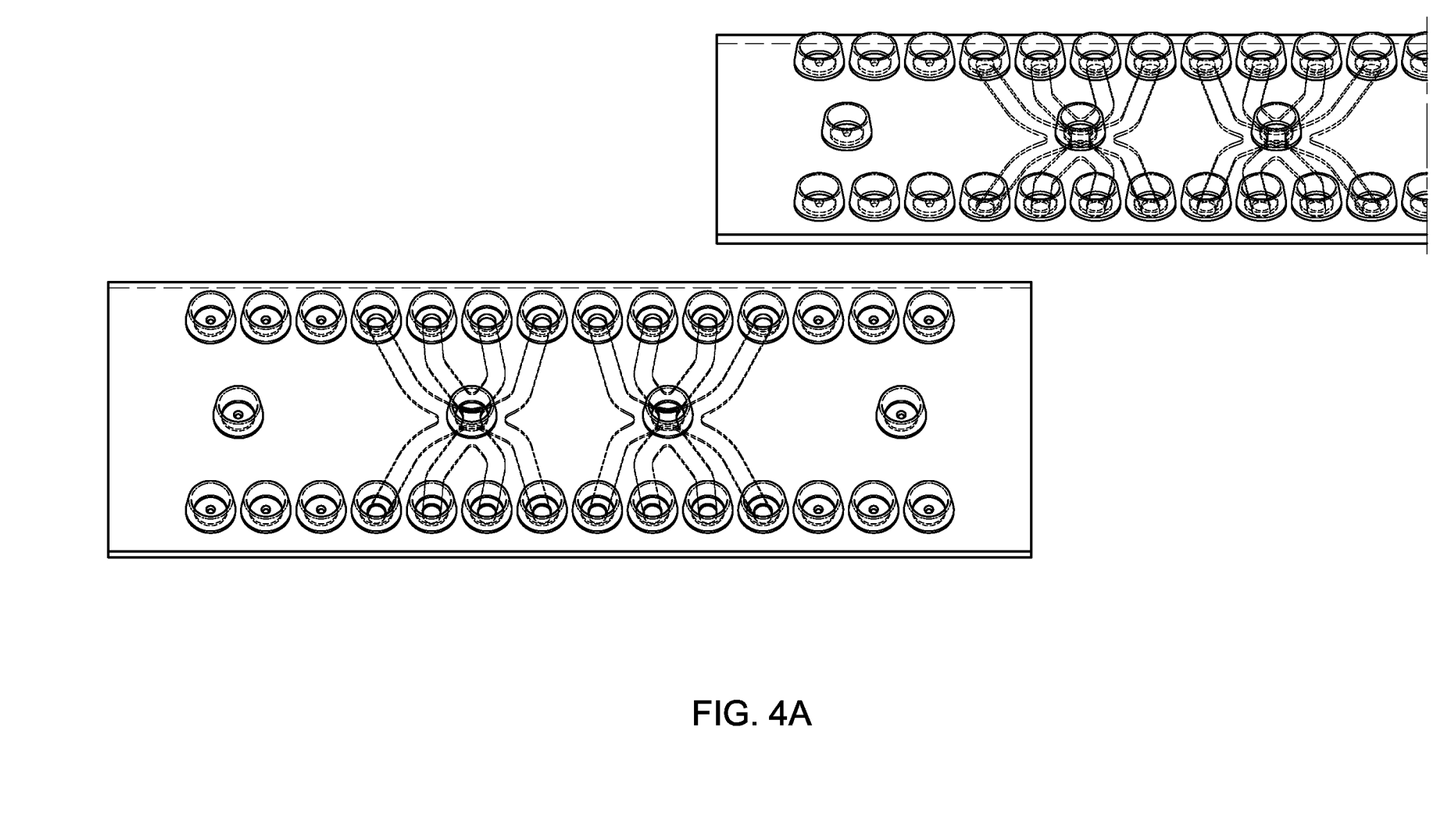
FIG. 4a shows a set of microfluidic devices in another embodiment according to the invention.
Figure 4B:
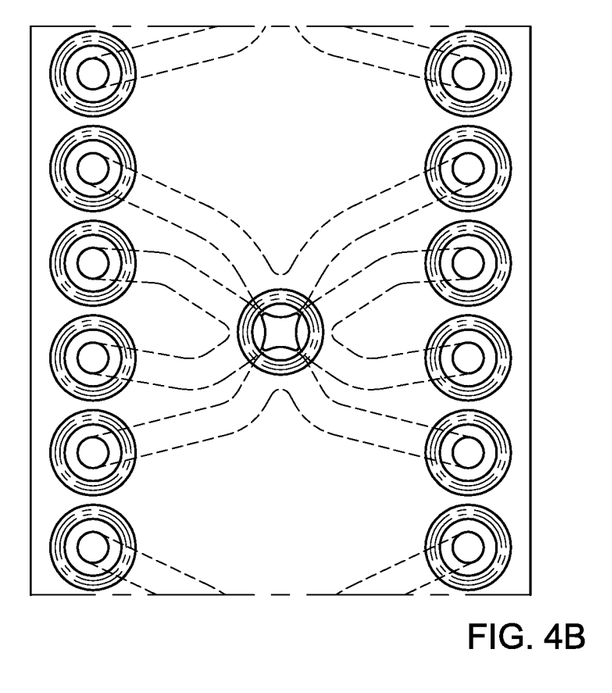
FIGS. 4b-4d show a detailed view of a microfluidic device according to the embodiment of FIG. 4a in respectively a top view, bottom view and enlarged view of a central part of the device.
Figure 4C:
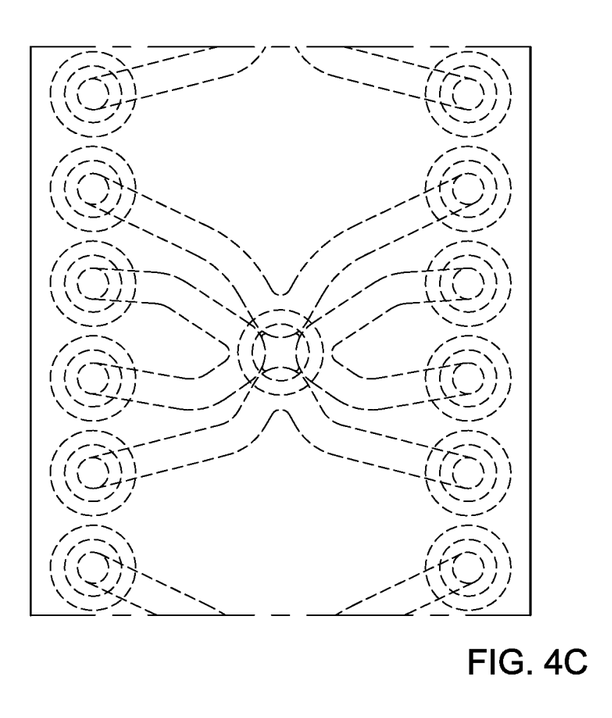
Figure 4D:
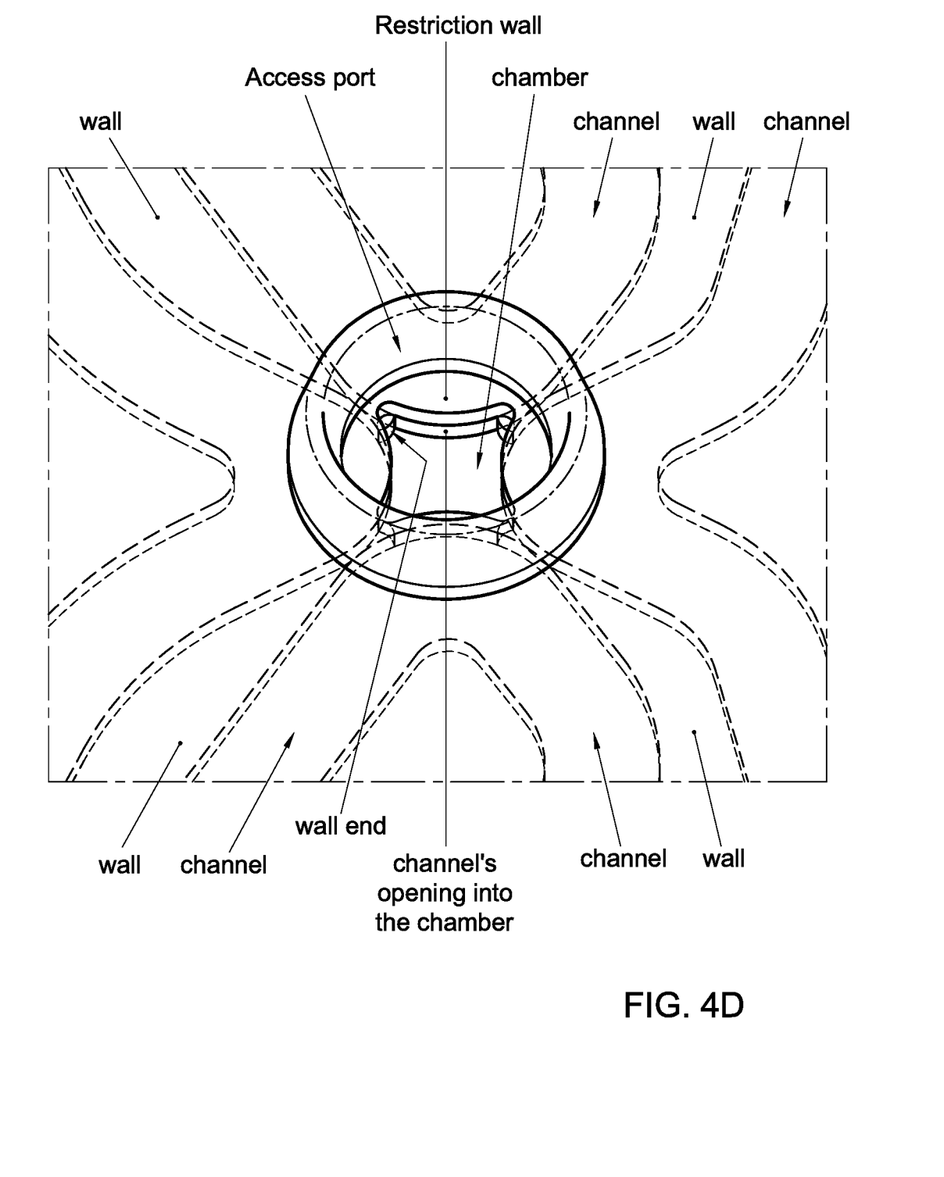

The microfluidic device according to the invention may be configured as a multiple units organ-on-a-chip. As shown in FIGS. 1-3 the microfluidic device comprises a body 1 which is substantially formed from PDMS in which each of the multiple units consists of three fluid paths 10, 20, 30 being configured as channels, each channel extending between a corresponding inlet port 11, 21, 31 at an outer surface of the body 2 and an outlet port 12, 22, 32. The channels accumulate in a central culture chamber 3 in the body 1. The culture chamber 3 is provided with a scaffolding substance in the form of a block of gel (hatched block in culture chamber 3 in FIG. 2). The block of gel is maintained in the culture chamber 3 resting on a bottom plate 2 of the body. The lateral sides of the block of gel are bound by the end parts of the walls 13, 23, 33 (FIG. 1 and FIG. 3) of the body separating the channels 10, 20, 30 from each other. The block of gel communicates with the channels for uptake of nutrients, metabolites, or other components or compounds from the fluid flowing through the channels by diffusion or perfusion. The flow is however directed from each inlet opening of each channel to each outlet opening of each channel along the block of gel, which poses a fluid flow barrier preventing direct flow of fluid into the culture chamber 3. The culture chamber 3 on an upper side opens into an access port 5 of the body 1, which access port is open at the outer top surface of the body 1. The access port 5 is provided directly above the culture chamber 3 so that the culture chamber is directly accessible from the outside through the access port. Between the access port 5 and the culture chamber 3 there is a restricting wall (FIG. 2) defining an opening between the culture chamber 3 and the access port 5 of which a cross sectional size is smaller than the cross sectional size of either the culture chamber 3 and the access port 5.

With this device the challenges of intestinal tissue engineering such as a coculture of different 2-D and 3-D cell types under well-defined conditions may be addressed. For example, a lumen-to-blood barrier of a human small intestine exists of 2-D cell types such as blood/lymphatic endothelial or intestinal epithelial cells and 3-D cell types such as different adherent and migrating cells of intestinal interstitium such as (myo)fibroblasts, neural and immune cells. In this regard direct contact of the fluid paths 10, 20, 30 with the scaffolding substance of the open access culture chamber 3 of the present embodiment allows: 1) 2-D cell culture of blood endothelial, lymph endothelial and intestinal epithelial cells under well-defined conditions on the scaffolding surface communicating with a particular fluid path; 2) 3-D cell culture within the scaffolding substance in the open access chamber; 3) direct mutual contact of all 2-D monolayers with the 3-D cell populated scaffolding including autocrine and paracrine cellular signaling and communications; 4) direct live imaging of cellular autocrine and paracrine communications via the bottom transparent plate 2 and/or the open access port 5 directly above, thus in line with, the culture chamber 3; 5) direct access and sampling from the 3-D cell populated scaffolding through the open access port above the culture chamber.

As an example a fully differentiated crypt-villus unit of intestinal epithelium of the human small intestine can reach 1.5 mm height. The larger fluid path 20 as compared to the smaller fluid paths 10, 30 of the body according to this embodiment due to its 3 mm width and 0.35 mm height allows fully 3-D development and differentiation of the crypt-villus unit in a parallel to a planar line direction in the microfluidic device.

Biomechanical and biochemical stimulation of cultured cells via different channels 10, 20, 30 with shear stress, pressure and biochemical stimuli allows in vitro simulation of some complex situations like for instance kinetic motion of plasma from blood capillary through interstitium into a lymphatic vessel; biochemical gradient of different compounds within interstitium like oxygen, different signaling molecules and metabolites; and cellular migration from a capillary, intestinal lumen of interstitium into lymphatic system. Separated fluid paths offer a formidable opportunity to sample medium (supernatant) for evaluation from different fluid paths.

In FIGS. 4a-4d an embodiment of a microfluidic device, particularly a chip, according to the invention is shown which is largely similar to the embodiment of FIGS. 1-3 but mainly differs in that instead of three fluid paths the body comprises four fluid paths which communicate with a culture chamber centrally located in the body. As particularly shown in FIG. 4a the microfluidic device comprises multiple culture chambers and corresponding access ports and fluid paths which form separate experimentation units. Accordingly the microfluidic chip may be used for multiple and/or parallel experiments. The four fluid paths are configured to communicate with the culture chamber at four different sides, approximately 90 degrees apart. The inlet and outlet openings of the fluid paths are all provided in the outer top surface of the body along the lateral ends thereof. The access ports are positioned more centrally and are aligned with respect to each other. The microfluidic device may be used in accordance with the foregoing description.

Interconnection of several units of the present embodiment in one microfluidic device, for example in one body such as a chip, allows creation of more complex systems such as a human digestive system (e.g. mouth-stomach-intestine) or a human body (e.g. intestine-liver-hart) using only one such microfluidic chip. Capabilities of this embodiment of the microfluidic device according to the invention can help to address the challenges not only in tissue and microfluidic engineering, but also in systems biology. The in vitro model provides experimentation for learning about the communication and control of biological systems at the scale of individual organs-on-chips. This complex, powerful, and integrated system allows recapitulating inter- and intra-organ signaling and dynamics of a human gastrointestinal tract.

Unless otherwise defined, all technical and scientific terms used herein have the same meaning as commonly understood by one of ordinary skill in the art to which this invention belongs. Methods and materials are described herein for use in the present invention. However other suitable methods and materials known in the art can also be used. The materials and examples are illustrative only and not intended to be limiting, unless so indicated. The following definitions are used unless otherwise described.

As used herein, the term "microfluidic device" refers to any device that allows for a precise control and manipulation of fluids that are constrained geometrically to a small, typically sub-millimeter, scale and is suitable for experimentation on cell cultures, particularly 3D cell cultures. The device is a tool that allows for control of the cellular environment. A particular embodiment of a microfluidic device as used herein is a microfluidic chip. A microfluidic device such as particularly a microfluidic chip is preferably made out of one or more of the materials SiO2, glass and synthetic polymers. As synthetic polymer a polysiloxane is preferred, and in particular polydimethylsiloxane (PDMS), although other polymers may be used, such as polycarbonate (PC), polystyrol (PS), polytetrafluoroethylene (PTFE) or cyclic olefin copolymer (COC). Particularly PDMS as material for microfluidic devices allows easy implementation of desired geometric structures and offers excellent live cell imaging conditions as PDMS is relatively transparent and has stable optical features, and particularly a low level of auto-fluorescence. Microfluidic cell culture devices made of PDMS therefore allow use of fluorescent live cell imaging, providing a powerful characterization of a multitude of cellular responses on a single cell as well as population level. Soft lithography of poly-dimethylsiloxane (PDMS) is a convenient method for the manufacturing of a microfluidic device for cell culture applications. With this technique, structures of micrometer resolution are molded from a hard master into PDMS. Such a microfluidic device allows for exact spatial and temporal control of fluid flow and delivery of media, drugs and signaling factors to live cells.

Although mixtures of two or more of the above materials may be employed for the device or parts of the device, it is preferred that the microfluidic device comprises at most a few different materials, and preferably is made at least almost wholly of a single material, for instance from COC which provides a high resistance against deforming of the body.

As used herein, the term "3D cell culture" refers to a cell culture with cells positioned relative to each other in three dimensions, i.e. width, depth and height. Such 3D cell culture for most cells better mimics cell to cell environments in tissues, organs and subjects. The microfluidic device according to the present invention is particularly suitable for culturing such 3D cell cultures, but may also be used for 2D cell cultures.

As used herein, the term "scaffolding substance" refers to any substance capable of maintaining living cells in a spatial relation in multiple dimensions, preferably 3 dimensions. Scaffolding substances may be liquids, gels or solids. Non limiting examples of scaffolding substance for use in a microfluidic device according to the invention are water, hydrogel, agar gel, micropore scaffold, microfiber scaffold, membrane and hollow fiber.

As used herein, the term "fluid" refers to any substance that continually flows under an applied shear stress. Fluids as used herein may include liquids, gases and plasmas.

As used herein, the term "fluid path" refers to any space through which a quantity of fluid may flow, such as a compartment, channel, chamber, or cavity.

For the purpose of clarity and a concise description, features are described herein as part of the same or separate aspects and preferred embodiments thereof, however, it will be appreciated that the scope of the invention may include embodiments having combinations of all or some of the features described.

The invention claimed is:

1. A microfluidic device for in vitro 3D cell culture experimentation comprising a body in which is provided:
   a cell culture chamber at least partly filled with a scaffolding substance for maintaining a cell culture; and
   a fluid path communicating with the cell culture chamber for directing a fluid stream along the scaffolding substance;
   wherein the culture chamber above the scaffolding substance opens into an access port provided at an outer top surface of the body for direct access to the scaffolding substance which forms a fluid flow barrier separating the fluid path from the access port, wherein the access port is provided directly above the cell culture chamber, and wherein the body comprises a restricting wall between the access port and the culture chamber, the restricting wall comprising at least one passage opening of which a cross sectional size is smaller than the cross section size of the culture chamber or the cross sectional size of the access port to restrict fluid communication between the access port and the culture chamber.

2. The microfluidic device according to claim 1, wherein the body comprises a set of fluid paths each fluid path communicating with the cell culture chamber for directing a respective fluid stream along the scaffolding substance, and the scaffolding substance separates the respective fluid paths.

3. The microfluidic device according to claim 1, wherein the fluid paths are channels in the body each channel extending between a respective inlet opening at an outer surface of the body and an outlet opening at an outer surface of the body.

4. The microfluidic device according to claim 3, wherein the access port has a height dimension extending between the outer top surface of the body and an opening to the culture chamber which height dimension is larger than a height dimension of the inlet opening of each channel extending between the outer surface of the body and a bottom of the respective channel.

5. The microfluidic device according claim 1, wherein the restricting wall defines a conical shaped access port.

6. The microfluidic device according to claim 1, wherein the scaffolding substance rests on a bottom part of the body opposite the outer top surface.

7. The microfluidic device according to claim 6, wherein the fluid paths communicate with the scaffolding substance at a lateral side of the culture chamber.

8. The microfluidic device according to claim 7, wherein the respective fluid paths communicate with the scaffolding substance at mutual different heights between the bottom part of the body and the outer top surface.

9. The microfluidic device according to claim 1, wherein at least one of the fluid paths has a larger communication area with the scaffolding substance as compared to another of the fluid paths.

10. The microfluidic device according to claim 1, wherein the body comprises at least three fluid paths.

11. The microfluidic device according to claim 10, wherein the three fluid paths communicate with the scaffolding substance at a respective lateral side of the culture chamber at approximately 120 degrees apart.

12. The microfluidic device according to claim 10, wherein at least one of the three fluid paths communicates with the scaffolding substance at a lower side of the culture chamber opposite the upper side.

13. The microfluidic device according to claim 1, wherein the fluid paths are separated along at least a part thereof by a wall of the body which wall has a wall end that borders the culture chamber and forms a support structure for the scaffolding substance.

14. The microfluidic device according to claim 13, wherein at least the wall end of the wall of the body is of a hydrophobic material.

15. The microfluidic device according to claim 13 wherein at least two wall ends of respective walls separating respective flow paths are positioned with respect to each other to define an imaginary circumference of the culture chamber and in that the scaffolding substance is bound by the imaginary circumference.

16. The microfluidic device according to claim 1, wherein the body is a microfluidic chip.

17. The microfluidic device according to claim 16, wherein the chip comprises multiple culture chambers and corresponding access ports and fluid paths.

18. The microfluidic device according to claim 17, wherein at least some of the fluid paths are shared between consecutive culture chambers.

19. The microfluidic device according to claim 1, wherein the body comprises a top plate with the outer top surface and a separate bottom plate with the bottom part which plates are adhered to each other.

20. The microfluidic device according to claim 19, wherein the bottom plate is at least almost fully flat.

21. The microfluidic device according to claim 1, wherein the fluid path of the microfluidic device has a height less than or equal to a total height of the scaffolding substance, with the body comprising a restricting element provided between the fluid path and scaffolding substance to restrict a communication surface between the fluid path and the scaffolding substance.

* * * * *